United States Patent
Weston et al.

(10) Patent No.: US 9,452,423 B2
(45) Date of Patent: Sep. 27, 2016

(54) MOLECULAR SIEVE MATERIAL, ITS SYNTHESIS AND USE

(71) Applicant: ExxonMobil Chemical Patents Inc., Baytown, TX (US)

(72) Inventors: Simon C. Weston, Annandale, NJ (US); Karl G. Strohmaier, Port Murray, NJ (US); Hilda B. Vroman, Piscataway, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 288 days.

(21) Appl. No.: 14/371,386

(22) PCT Filed: Dec. 27, 2012

(86) PCT No.: PCT/US2012/071819
§ 371 (c)(1),
(2) Date: Jul. 9, 2014

(87) PCT Pub. No.: WO2013/126140
PCT Pub. Date: Aug. 29, 2013

(65) Prior Publication Data
US 2015/0025291 A1     Jan. 22, 2015

Related U.S. Application Data

(60) Provisional application No. 61/601,187, filed on Feb. 21, 2012.

(30) Foreign Application Priority Data

Apr. 18, 2012   (EP) .................................. 12164538

(51) Int. Cl.
*C01B 39/08* (2006.01)
*C01B 39/48* (2006.01)
*B01J 29/70* (2006.01)
*C01B 37/00* (2006.01)
*C01B 37/02* (2006.01)
*C07C 2/00* (2006.01)
*C07C 4/06* (2006.01)
*C07C 5/22* (2006.01)
*C07C 6/00* (2006.01)

(52) U.S. Cl.
CPC .............. *B01J 29/70* (2013.01); *C01B 37/007* (2013.01); *C01B 37/02* (2013.01); *C01B 39/08* (2013.01); *C01B 39/48* (2013.01); *C07C 2/00* (2013.01); *C07C 4/06* (2013.01); *C07C 5/222* (2013.01); *C07C 6/00* (2013.01)

(58) Field of Classification Search
CPC ..... C01B 39/08; C01B 39/48; C01B 37/007; C01B 37/02; B01J 29/70
See application file for complete search history.

(56) References Cited

U.S. PATENT DOCUMENTS

| | | | |
|---|---|---|---|
| 4,391,785 A | 7/1983 | Rosinski et al. | |
| 5,108,579 A | 4/1992 | Casci | |
| 6,337,428 B1 | 1/2002 | Benazzi et al. | |
| 6,524,551 B2 | 2/2003 | Dhingra | |
| 7,063,828 B2 * | 6/2006 | Burton, Jr. ............... | B01J 29/06 423/706 |
| 7,442,366 B2 * | 10/2008 | Mueller ................ | C01B 37/005 423/702 |
| 8,629,073 B2 * | 1/2014 | Guillon .................... | B01J 29/72 502/60 |
| 8,936,717 B2 * | 1/2015 | Guillon .................... | B01J 29/76 208/108 |
| 9,327,277 B2 * | 5/2016 | Yang ........................ | B01J 29/70 |
| 2002/0164284 A1 | 11/2002 | Dhingra | |
| 2015/0025291 A1 | 1/2015 | Weston et al. | |
| 2015/0202612 A1 * | 7/2015 | Schmidt .................. | B01J 29/70 585/640 |

FOREIGN PATENT DOCUMENTS

| | | |
|---|---|---|
| CN | 1058196 | 1/1992 |
| JP | H03-122009 | 10/1992 |
| JP | H05-97429 | 10/1994 |
| JP | H07-503693 | 4/1995 |
| WO | 2013/126140 | 8/2013 |

OTHER PUBLICATIONS

Baerlocher et al., *Atlas of Zeolite Framework Types*, Elsevier, Sixth Revised Edition, 2007.
Shannon, *"Method of Solution and Structure of 3 Novel High-Silica Medium-Pore Zeolites with Multi-Dimensional Channel Systems"*, Proceedings from the Ninth International Zeolite Conference, ed. by R. Von Ballmoos, J.B. Higgins and M.M.J. Treacy, Butterworth-Heinemann, Stoneham, MA, pp. 389-398, 1993.

\* cited by examiner

*Primary Examiner* — David M Brunsman
(74) *Attorney, Agent, or Firm* — Darryl M. Tyus

(57) ABSTRACT

A molecular sieve material, EMM-17, has in its as-calcined form an X-ray diffraction pattern including the following peaks in Table 11:

TABLE 11

| d-spacing (Å) | Relative Intensity [100 × I/I(o)] % |
|---|---|
| 17.4-16.4 | 1-10 |
| 12.6-12.1 | 1-20 |
| 11.8-11.4 | 60-100 |
| 11.2-10.8 | 5-30 |
| 10.7-10.3 | 30-80 |
| 8.62-8.38 | 10-40 |
| 6.09-5.96 | 1-20 |
| 5.71-5.61 | 1-20 |
| 4.23-4.17 | 1-20 |
| 4.09-4.03 | 1-10 |
| 3.952-3.901 | 10-40 |
| 3.857-3.809 | 5-30 |
| 3.751-3.705 | 1-20 |
| 3.727-3.682 | 1-20 |
| 3.689-3.644 | 1-10 |
| 3.547-3.506 | 1-20 |

15 Claims, 2 Drawing Sheets

MOLECULAR SIEVE MATERIAL, ITS SYNTHESIS AND USE

CROSS REFERENCE TO RELATED APPLICATIONS

This application is a national stage application under 35 USC 371 of International Application No. PCT/US2012/071819, filed Dec. 27, 2012, which claims the benefits of and priorities to U.S. Provisional Application Ser. No. 61/601,187, filed Feb. 21, 2012, and European Application No. 12164538.6, filed Apr. 18, 2012, the disclosures of which are fully incorporated herein by reference in their entireties.

FIELD

This invention relates to a novel molecular sieve material, designated EMM-17, its synthesis and its use as an adsorbent and as a catalyst for hydrocarbon conversion reactions.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum) being balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

One known intermediate pore size zeolite is NU-86, the synthesis of which in the presence of a polymethylene alpha, omega-diammonium cation is disclosed in U.S. Pat. No. 5,108,579 to J. L. Casci. The proposed structure of NU-86 has a three dimensional pore system including one set of straight channels defined by a ring of 11 oxygen and 11 tetrahedral atoms, one set of straight channels defined by a ring of alternating 10 and 12 oxygen and alternating 10 and 12 tetrahedral atoms and one set of sinusoidal channels defined by a ring of alternating 10 and 12 oxygen and alternating 10 and 12 tetrahedral atoms (see M. D. Shannon, "Method of solution and structure determination of 3 novel high-silica medium-pore zeolites with multi-dimensional channel systems", *Proceedings of the Ninth International Zeolite Conference*, ed. by R. von Ballmoos, J. B. Higgins, and M. M. J. Treacy, Butterworth-Heinemann, Stoneham, Mass., 1993, pp 389-398). NU-86 has been shown to have utility in the oligomerization of $C_2$-$C_8$ olefins (see U.S. Pat. No. 6,337,428).

According to the present invention, a new zeolite structure, designated EMM-17, has now been synthesized using at least one of the following four organic templates: 1-methyl-4-(pyrrolidin-1-yl)pyridinium cations, 1-ethyl-4-(pyrrolidin-1-yl)pyridinium cations, 1-propyl-4-(pyrrolidin-1-yl)pyridinium cations, and 1-butyl-4-(pyrrolidin-1-yl)pyridinium cations. The new zeolite has an X-ray diffraction (XRD) pattern that is similar to, but distinguished from, that of NU-86 and possesses a high micropore volume of 11.3%, as determined by n-hexane sorption.

SUMMARY

In one aspect, the invention resides in a molecular sieve material having, in its as-calcined form, an X-ray diffraction pattern including the following peaks in Table 1:

TABLE 1

| d-spacing (Å) | Relative Intensity [100 × I/I(o)] % |
| --- | --- |
| 17.4-16.4 | 1-10 |
| 12.6-12.1 | 1-20 |
| 11.8-11.4 | 60-100 |
| 11.2-10.8 | 5-30 |
| 10.7-10.3 | 30-80 |
| 8.62-8.38 | 10-40 |
| 6.09-5.96 | 1-20 |
| 5.71-5.61 | 1-20 |
| 4.23-4.17 | 1-20 |
| 4.09-4.03 | 1-10 |
| 3.952-3.901 | 10-40 |
| 3.857-3.809 | 5-30 |
| 3.751-3.705 | 1-20 |
| 3.727-3.682 | 1-20 |
| 3.689-3.644 | 1-10 |
| 3.547-3.506 | 1-20 |

Conveniently, the molecular sieve material has a composition comprising the molar relationship:

$X_2O_3:(n)YO_2$ wherein n is at least 30, X is a trivalent element, such as one or more of B, Al, Fe, and Ga, especially Al, and Y is a tetravalent element, such as one or more of Si, Ge, Sn, Ti, and Zr, especially Si.

In another aspect, the invention resides in a molecular sieve material having, in its as-synthesized form, an X-ray diffraction pattern including the following peaks in Table 2:

TABLE 2

| d-spacing (Å) | Relative Intensity [100 × I/I(o)] % |
|---|---|
| 17.3-16.4 | 1-10 |
| 11.8-11.3 | 60-100 |
| 11.1-10.7 | 60-100 |
| 10.7-10.3 | 30-100 |
| 8.58-8.34 | 30-80 |
| 4.21-4.15 | 10-40 |
| 4.17-4.11 | 5-30 |
| 4.07-4.01 | 10-40 |
| 3.951-3.899 | 60-100 |
| 3.922-3.871 | 10-40 |
| 3.832-3.784 | 50-90 |
| 3.737-3.691 | 10-40 |
| 3.704-3.659 | 10-40 |
| 3.677-3.632 | 5-30 |
| 3.537-3.496 | 10-40 |
| 2.077-2.063 | 5-30 |

Conveniently, the molecular sieve material has a composition comprising the molar relationship:

$kF:mQ:(n)YO_2: X_2O_3$ wherein $0 \leq k \leq 1.0$, $0 < m \leq 1.0$, n is at least 30, F is fluoride, Q is an organic structure directing agent, X is a trivalent element and Y is a tetravalent element.

In embodiments, X may be one or more of B, Al, Fe, Ga and Al; and Y may be one or more of Si, Ge, Sn, Ti and Zr.

Conveniently, Q comprises at least one of 1-methyl-4-(pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations, and mixtures thereof.

In a further aspect, the invention resides in a process for producing the molecular sieve material as described herein, the process comprising:

(i) preparing a synthesis mixture capable of forming said material, said mixture comprising water, a source of hydroxyl ions, a source of an oxide of a tetravalent element Y, optionally a source of a trivalent element X, optionally a source of fluoride ions, and a directing agent Q selected from the group consisting of 1-methyl-(4-pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations and mixtures thereof, and said synthesis mixture having a composition, in terms of mole ratios, in the following amounts and/or ranges:

$YO_2/X_2O_3$ at least 30;

$H_2O/YO_2$ 4 to 10;

$OH^-/YO_2$ 0.1 to 1;

$F/YO_2$ 0 to 1; and $Q/YO_2$ 0.1 to 1;

(ii) heating said synthesis mixture under crystallization conditions including a temperature of from about 100° C. to about 200° C. and a time from about 1 to about 28 days until crystals of said material are formed; and (iii) recovering said crystalline material from step (ii).

In another aspect, the invention resides in a process for synthesizing a crystalline molecular sieve material comprising providing a synthesis mixture capable of forming the crystalline molecular sieve material, including in said mixture an organic directing agent selected from the group consisting of 1-methyl-(4-pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations and mixtures thereof, and heating said synthesis mixture under crystallization conditions until crystals of said molecular sieve material are formed containing said organic directing agent within the crystalline structure of the molecular sieve material.

DETAILED DESCRIPTION OF EMBODIMENTS

Figure 1:
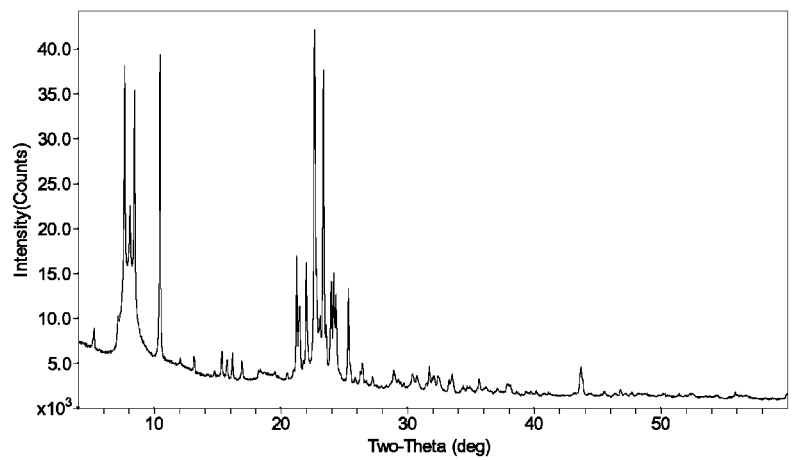
FIG. 1 shows the X-ray diffraction pattern of the synthesized zeolite of Example 5.

Described herein is a novel molecular sieve material, which is designated EMM-17, its synthesis in the presence of a structure directing agent, and its use as an adsorbent and a catalyst for organic conversion reactions.

The novel molecular sieve material EMM-17 is characterized by an X-ray diffraction pattern which, in the as-calcined form of the molecular sieve, includes at least the peaks shown below in Table 3; and in the as-synthesized form, includes at least the peaks shown below in Table 4.

TABLE 3

| X-Ray Diffraction Pattern of As-Calcined Form of EMM-17 ||
|---|---|
| d-spacing (Å) | Relative Intensity [100 × I/I(o)] % |
| 17.4-16.4 | 1-10 |
| 12.6-12.1 | 1-20 |
| 11.8-11.4 | 60-100 |
| 11.2-10.8 | 5-30 |
| 10.7-10.3 | 30-80 |
| 8.62-8.38 | 10-40 |
| 6.09-5.96 | 1-20 |
| 5.71-5.61 | 1-20 |
| 4.23-4.17 | 1-20 |
| 4.09-4.03 | 1-10 |
| 3.952-3.901 | 10-40 |
| 3.857-3.809 | 5-30 |
| 3.751-3.705 | 1-20 |
| 3.727-3.682 | 1-20 |
| 3.689-3.644 | 1-10 |
| 3.547-3.506 | 1-20 |

TABLE 4

X-Ray Diffraction Pattern of As-Synthesized Form of EMM-17

| d-spacing (Å) | Relative Intensity [100 × I/I(o)] % |
|---|---|
| 17.3-16.4 | 1-10 |
| 11.8-11.3 | 60-100 |
| 11.1-10.7 | 60-100 |
| 10.7-10.3 | 30-100 |
| 8.58-8.34 | 30-80 |
| 4.21-4.15 | 10-40 |
| 4.17-4.11 | 5-30 |
| 4.07-4.01 | 10-40 |
| 3.951-3.899 | 60-100 |
| 3.922-3.871 | 10-40 |
| 3.832-3.784 | 50-90 |
| 3.737-3.691 | 10-40 |
| 3.704-3.659 | 10-40 |
| 3.677-3.632 | 5-30 |
| 3.537-3.496 | 10-40 |
| 2.077-2.063 | 5-30 |

The X-ray diffraction data reported herein were collected with a PANalytical X-Pert Pro diffraction system, equipped with an X'Celerator detector, using copper K-alpha radiation and a fixed 0.25 degrees divergence slit. The diffraction data were recorded by step-scanning at 0.017 degrees of two-theta, where theta is the Bragg angle, and a counting time of 20 seconds for each step. The interplanar spacings, d-spacings, were calculated in Angstrom units, and the relative peak area intensities of the lines, $I/I_{(o)}$ is one-hundredth of the intensity of the strongest line, above background, were determined with the MDI Jade peak profile fitting algorithm. The intensities are uncorrected for Lorentz and polarization effects. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

The molecular sieve material EMM-17, in its as-calcined form, has a chemical composition having the following molar relationship:

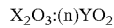

$X_2O_3:(n)YO_2$ wherein n is at least about 30, such as about 30 to about 200, X is a trivalent element, such as one or more of B, Al, Fe, and Ga, and Y is a tetravalent element, such as one or more of Si, Ge, Sn, Ti, and Zr. It will be appreciated from permitted values for n that EMM-17 can be synthesized in an all siliceous form, in which the trivalent element X is absent or effectively absent.

In its as-synthesized form, molecular sieve EMM-17 has a chemical composition having the following molar relationship:

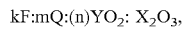

$kF:mQ:(n)YO_2: X_2O_3$, wherein $0 \leq k \leq 1.0$, $0 < m \leq 1.0$, n is at least 30, F is fluoride, Q is an organic structure directing agent, X is a trivalent element, such as one or more of B, Al, Fe, and Ga, and Y is a tetravalent element, such as one or more of Si, Ge, Sn, Ti, and Zr.

In embodiments, suitable examples of the organic structure directing agent Q include 1-methyl-4-(pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations, and mixtures thereof.

The Q and F components, which are associated with the as-synthesized form of molecular sieve EMM-17 as a result of their presence during crystallization, may be easily removed by conventional post-crystallization methods.

The molecular sieve material EMM-17 is a thermally stable zeolite with a unique XRD pattern and, in its calcined form, typically has high micropore volume of 11.4%, as determined by n-hexane sorption.

EMM-17 can be prepared from a synthesis mixture comprising a source of water, a source of hydroxyl ions, an oxide of a tetravalent element Y, optionally a trivalent element X, optionally a source fluoride ions F, and a directing agent Q described above. The synthesis mixture may have a composition, in terms of mole ratios of oxides, within the following amounts and/or ranges:

| Reactants | Useful | Preferred |
|---|---|---|
| $YO_2/X_2O_3$ | at least 30 | 30 to 200 |
| $H_2O/YO_2$ | 1 to 20 | 4 to 10 |
| $OH^-/YO_2$ | 0.1 to 1 | 0.3 to 0.7 |
| $F/YO_2$ | 0.1 to 1 | 0.3 to 0.7 |
| $Q/YO_2$ | 0.1 to 1 | 0.3 to 0.7 |

Suitable sources of tetravalent element Y depend on the element Y that is selected (e.g., silicon, germanium, strontium, titanium and zirconium). In embodiments where Y is silicon, suitable sources of silicon include colloidal suspensions of silica, precipitated silica alkali metal silicates, and tetraalkyl orthosilicates. In embodiments where Y is germanium, germanium oxide may be used as an oxide source.

If present, suitable sources of trivalent element X depend on the element X that is selected (e.g., boron, aluminum, iron and gallium. In embodiments where X is aluminum, sources of aluminum include hydrated alumina and water-soluble aluminum salts, such as aluminum nitrate.

If present, suitable sources of fluoride ions include HF, $NH_4F$ and $NH_4HF_2$.

Suitable sources of the directing agent Q include the hydroxides and/or salts of the relevant quaternary ammonium compounds. 1-Methyl-4-(pyrrolidin-1-yl)pyridinium compounds can be readily synthesized by the reaction of 4-(pyrrolidin-1-yl)pyridine with iodomethane. 1-Ethyl-4-(pyrrolidin-1-yl)pyridinium compounds can be readily synthesized by the reaction of 4-(pyrrolidin-1-yl)pyridine with iodoethane. 1-Propyl-4-(pyrrolidin-1-yl)pyridinium compounds can be readily synthesized by the reaction of 4-(pyrrolidin-1-yl)pyridine with 1-iodopropane. 1-Butyl-4-(pyrrolidin-1-yl)pyridinium compounds can be readily synthesized by the reaction of 4-(pyrrolidin-1-yl)pyridine with 1-iodobutane.

Crystallization of EMM-17 can be carried out at either static or stirred conditions in a suitable reactor vessel, such as for example, polypropylene jars or Teflon lined or stainless steel autoclaves, at a temperature of about 100° C. to about 200° C., such as about 150° C. to about 170° C., for a time sufficient for crystallization to occur at the temperature used, e.g., from about 1 day to about 30 days, for example about 2 days to about 20 days. Thereafter, the synthesized crystals are separated from the liquid and recovered.

The synthesis may be aided by seeds from a previous synthesis of EMM-17, with the seeds suitably being present in an amount from about 0.01 ppm by weight to about 10,000 ppm by weight, such as from about 100 ppm by weight to about 5,000 ppm by weight of the synthesis mixture.

To the extent desired and depending on the $X_2O_3/YO_2$ molar ratio of the material, any cations in the as-synthesized EMM-17 can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The molecular sieve described herein may be subjected to treatment to remove a portion of or the entire amount of organic directing agent Q used in its synthesis. This is conveniently done by thermal treatment (calcination) in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

The molecular sieve described herein may be intimately combined with a hydrogenating component, such as molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The molecular sieve of the present disclosure, when employed either as an adsorbent or as a catalyst should be dehydrated, at least partially. This can be done by heating to a temperature in the range of about 100° C. to about 500° C., such as about 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the EMM-17 in a vacuum, but a longer time is required to obtain a sufficient amount of dehydration.

The molecular sieve of the present disclosure may be used as an adsorbent or, particularly in its aluminosilicate form, as a catalyst to catalyze a wide variety of organic compound conversion processes including many of present commercial/industrial importance. Examples of chemical conversion processes which are effectively catalyzed by the crystalline material of this invention, by itself or in combination with one or more other catalytically active substances including other crystalline catalysts, include those requiring a catalyst with acid activity. Examples of organic conversion processes which may be catalyzed by EMM-17 include cracking, hydrocracking, disproportionation, alkylation, and isomerization.

As in the case of many catalysts, it may be desirable to incorporate EMM-17 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with EMM-17, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with EMM-17 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with EMM-17 also include inorganic oxides, such as silica, zirconia, titania, magnesia, beryllia, alumina, and mixtures thereof In addition to the foregoing materials, EMM-17 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of EMM-17 and inorganic oxide matrix may vary widely, with the EMM-17 content ranging from about 1 to about 90 percent by weight and more usually, particularly when the composite is prepared in the form of beads, in the range of about 2 to about 80 weight percent of the composite.

The invention will now be more particularly described with reference to the following non-limiting Examples and the accompanying drawings.

Example 1A

Synthesis of 1-methyl-4-(pyrrolidin-1-yl)pyridinium iodide

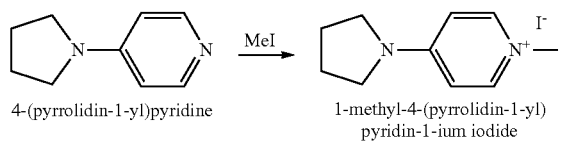

4-(pyrrolidin-1-yl)pyridine → 1-methyl-4-(pyrrolidin-1-yl)pyridin-1-ium iodide

Iodomethane (156.13 g) was added to a solution of 4-(pyrrolidin-1-yl)pyridine (148.20 g) dissolved in ethanol (584 ml). The reaction mixture was stirred for 30 minutes and then refluxed for at least 5 hours whereupon the reaction product was allowed to precipitate by cooling to at least room temperature. The solid product was then filtered and washed with cold ethanol. After drying the product (267.09 g, 92%) was confirmed to be 1-methyl-4-(pyrrolidin-1-yl)pyridinium iodide by $^1$H NMR in $D_2O$.

Example 1B

Synthesis of 1-methyl-4-(pyrrolidin-1-yl)pyridinium hydroxide 1-methyl-4-(pyrrolidin-1-yl)pyridinium iodide produced in Example 1A was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically about 20 wt. %. The concentration was confirmed by acid-base titration and by $^1$H NMR in $D_2O$.

Example 2A

Synthesis of 1-ethyl-4-(pyrrolidin-1-yl)pyridinium iodide

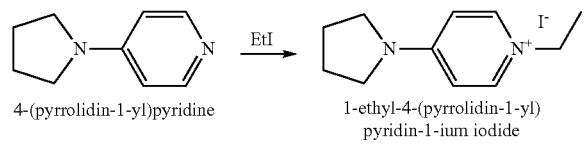

4-(pyrrolidin-1-yl)pyridine → 1-ethyl-4-(pyrrolidin-1-yl)pyridin-1-ium iodide

Iodoethane (85.78 g) was added to a solution of 4-(pyrrolidin-1-yl)pyridine (74.10 g) dissolved in ethanol (73 ml). The reaction mixture was stirred for 30 minutes and then refluxed for at least 5 hours whereupon the reaction product was allowed to precipitate by cooling to less than 10° C. The solid product was then filtered. After drying, the product (150.32 g, 69%) was confirmed to be 1-ethyl-4-(pyrrolidin-1-yl)pyridinium iodide by $^1$H NMR in $D_2O$.

Example 2B

Synthesis of 1-ethyl-4-(pyrrolidin-1-yl)pyridinium hydroxide 1-ethyl-4-(pyrrolidin-1-yl)pyridinium iodide produced in Example 2A was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically about 20 wt. %. The concentration was confirmed by acid-base titration and by $^1$H NMR in $D_2O$.

Example 3A

Synthesis of 1-propyl-4-(pyrrolidin-1-yl)pyridinium iodide

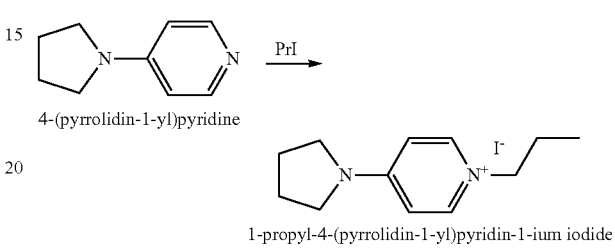

4-(pyrrolidin-1-yl)pyridine → 1-propyl-4-(pyrrolidin-1-yl)pyridin-1-ium iodide

1-Iodopropane (56.10 g) was added to a solution of 4-(pyrrolidin-1-yl)pyridine (44.46 g) dissolved in ethanol (88 ml). The reaction mixture was stirred for 30 minutes and then refluxed for at least 5 hours whereupon the reaction product was allowed to precipitate by cooling to at least room temperature. The solid product was then filtered and washed with cold ethanol. After drying the product (84.87 g, 89%) was confirmed to be 1-propyl-4-(pyrrolidin-1-yl)pyridinium iodide by $^1$H NMR in $D_2O$.

Example 3B

Synthesis of 1-propyl-4-(pyrrolidin-1-yl)pyridinium hydroxide 1-propyl-4-(pyrrolidin-1-yl)pyridinium iodide produced in Example 3A was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically about 20 wt. %. The concentration was confirmed by acid-base titration and by $^1$H NMR in $D_2O$.

Example 4A

Synthesis of 1-butyl-4-(pyrrolidin-1-yl)pyridinium iodide

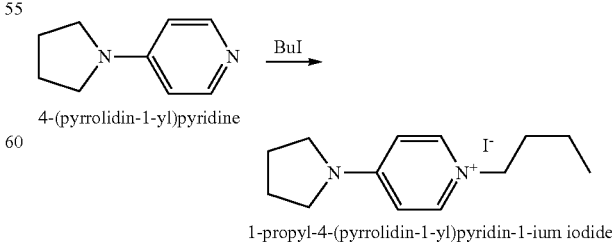

4-(pyrrolidin-1-yl)pyridine → 1-propyl-4-(pyrrolidin-1-yl)pyridin-1-ium iodide

1-Iodobutane (60.73 g) was added to a solution of 4-(pyrrolidin-1-yl)pyridine (44.46 g) dissolved in ethanol (88 ml).

The reaction mixture was stirred for 30 minutes and then refluxed for at least 5 hours whereupon the reaction product was allowed to precipitate by cooling to at least room temperature. The solid product was then filtered and washed with cold ethanol. After drying the product (86.83 g, 87%) was confirmed to be 1-butyl-4-(pyrrolidin-1-yl)pyridinium iodide by $^1$H NMR in $D_2O$.

Example 4B

Synthesis of 1-butyl-4-(pyrrolidin-1-yl)pyridinium hydroxide 1-butyl-4-(pyrrolidin-1-yl)pyridinium iodide was subsequently converted to a hydroxide solution by column ion-exchange using an excess of MTO-DOWEX SBR LCNG (OH) resin. Distilled water was eluted through the column until the pH was less than 11 and the resulting solution concentrated to the desired concentration, typically about 20 wt. %. The concentration was confirmed by acid-base titration and by $^1$H NMR in $D_2O$.

Example 5

Synthesis of EMM-17

A gel of stoichiometry: 0.5 HF: 0.5 SDA-OH: $SiO_2$: 4 $H_2O$ was prepared according to the following procedure. 14.3 g tetramethylorthosilicate was combined with 35.7 g of a 23.8 wt. % aqueous solution of 1-methyl-4-(pyrrolidin-1-yl)pyridinium hydroxide, and stirred overnight under a mild nitrogen purge. A stiff gel was formed, which was broken up with a spatula. The gel was allowed to dry for one more day until the weight reduced to 16.7 g. The dried gel was then ground into a coarse powder, to which 4.7 g of a 20 wt. % aqueous solution of hydrofluoric acid was added, along with 0.3 ml deionized water, to form a gel. The resulting gel was thoroughly mixed with a spatula for 5 minutes and then transferred to two Teflon lined autoclaves and reacted at 160° C. for 8 days in a tumbling (40 rpm) oven. The product was recovered by filtration, washed thoroughly with deionized water and then dried at 115° C. in an oven. The resulting product of Example 5 was analyzed by powder X-ray diffraction and shown to be pure EMM-17 (see FIG. 1).

The X-ray diffraction peaks of the synthesized product of Example 5 are shown below in Table 5. The X-ray diffraction pattern was measured with copper Kα radiation on a PANalytical X'Pert Pro diffractometer equipped with an X'celerator detector and a fixed 0.25 degrees divergence slit. Peak positions and intensities (peak area) were calculated using MDI Jade profile fitting routine.

TABLE 5

X-Ray Diffraction Pattern of the As-Synthesized EMM-17 of Example 5

| 2Θ | d (Å) | Relative Intensity [100 × I/I(o)] % |
|---|---|---|
| 5.24 | 16.85 | 5 |
| 7.12 | 12.32 | 9 |
| 7.66 | 11.53 | 100 |
| 8.08 | 10.94 | 84 |
| 8.44 | 10.47 | 94 |
| 10.45 | 8.46 | 64 |
| 12.04 | 7.35 | 2 |
| 13.14 | 6.73 | 3 |
| 14.74 | 6.00 | 2 |
| 15.33 | 5.774 | 7 |
| 15.74 | 5.625 | 5 |
| 16.17 | 5.476 | 6 |
| 16.91 | 5.238 | 4 |
| 18.29 | 4.847 | 5 |
| 18.67 | 4.748 | 5 |
| 19.01 | 4.664 | 3 |
| 19.46 | 4.557 | 5 |
| 20.47 | 4.335 | 1 |
| 20.96 | 4.235 | 1 |
| 21.23 | 4.182 | 28 |
| 21.44 | 4.141 | 17 |
| 21.99 | 4.039 | 27 |
| 22.64 | 3.925 | 91 |
| 22.80 | 3.897 | 21 |
| 23.08 | 3.851 | 11 |
| 23.34 | 3.808 | 75 |
| 23.56 | 3.773 | 7 |
| 23.94 | 3.714 | 23 |
| 24.16 | 3.681 | 24 |
| 24.34 | 3.655 | 19 |
| 25.31 | 3.517 | 21 |
| 25.46 | 3.495 | 3 |
| 25.84 | 3.445 | 1 |
| 26.28 | 3.389 | 3 |
| 26.42 | 3.371 | 5 |
| 27.21 | 3.274 | 2 |
| 28.33 | 3.148 | 1 |
| 28.90 | 3.088 | 9 |
| 29.22 | 3.054 | 3 |
| 29.43 | 3.033 | 2 |
| 29.70 | 3.005 | 2 |
| 30.36 | 2.942 | 8 |
| 30.72 | 2.908 | 7 |
| 31.44 | 2.843 | 1 |
| 31.70 | 2.820 | 9 |
| 32.03 | 2.792 | 7 |
| 32.41 | 2.760 | 8 |
| 33.28 | 2.690 | 3 |
| 33.51 | 2.672 | 7 |
| 34.37 | 2.607 | 2 |
| 34.69 | 2.584 | 2 |
| 34.91 | 2.568 | 2 |
| 35.63 | 2.518 | 6 |
| 36.13 | 2.484 | 3 |
| 37.09 | 2.422 | 3 |
| 37.86 | 2.374 | 5 |
| 38.09 | 2.361 | 4 |
| 38.62 | 2.329 | 1 |
| 39.36 | 2.288 | 2 |
| 39.72 | 2.267 | 2 |
| 43.69 | 2.070 | 13 |

Example 6

Calcination of the EMM-17 Synthesized in Example 5

Figure 2:
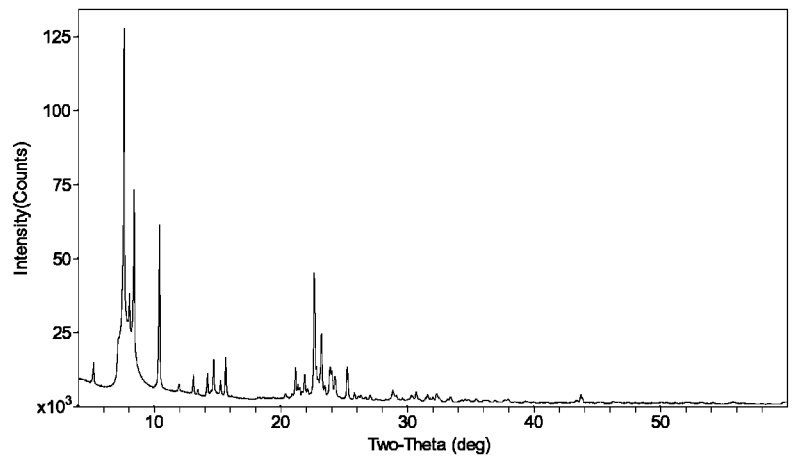
FIG. 2 shows the X-ray diffraction pattern of the calcined zeolite of Example 17.

A 1 g sample of EMM-17 from Example 5 was calcined in a furnace by heating the sample in air from room temperature to 600° C. for two hours, and then holding the temperature at 600° C. for 5 hours to obtain a white solid powder. The as-calcined product of Example 6 was shown to be pure EMM-17 by powder X-ray diffraction analysis (see FIG. 2). The X-ray diffraction peaks are shown below in Table 6, taken at conditions corresponding to those found in Example 5.

TABLE 6

X-Ray Diffraction Pattern of As-Calcined EMM-17 of Example 2

| 2Θ | d (Å) | Relative Intensity [100 × I/I(o)] % |
|---|---|---|
| 5.22 | 16.9 | 3 |
| 7.18 | 12.31 | 9 |
| 7.62 | 11.60 | 100 |
| 8.04 | 10.98 | 16 |
| 8.40 | 10.52 | 53 |
| 10.40 | 8.50 | 23 |
| 11.96 | 7.39 | 2 |
| 13.08 | 6.762 | 3 |
| 14.19 | 6.237 | 3 |
| 14.69 | 6.024 | 7 |
| 15.24 | 5.811 | 3 |
| 15.64 | 5.660 | 7 |
| 16.23 | 5.458 | 1 |
| 20.34 | 4.363 | 1 |
| 21.14 | 4.199 | 5 |
| 21.34 | 4.160 | 2 |
| 21.47 | 4.135 | 1 |
| 21.87 | 4.062 | 4 |
| 22.09 | 4.020 | 1 |
| 22.63 | 3.926 | 23 |
| 22.81 | 3.895 | 4 |
| 22.96 | 3.871 | 2 |
| 23.19 | 3.833 | 13 |
| 23.46 | 3.790 | 2 |
| 23.85 | 3.728 | 6 |
| 24.00 | 3.705 | 5 |
| 24.26 | 3.667 | 5 |
| 25.23 | 3.527 | 6 |
| 25.81 | 3.449 | 2 |
| 26.11 | 3.410 | 1 |
| 26.32 | 3.383 | 1 |
| 26.65 | 3.342 | 1 |
| 27.04 | 3.295 | 2 |
| 27.49 | 3.242 | 1 |
| 28.82 | 3.095 | 3 |
| 29.08 | 3.068 | 2 |
| 29.59 | 3.016 | 1 |
| 30.32 | 2.946 | 2 |
| 30.69 | 2.911 | 3 |
| 31.57 | 2.832 | 2 |
| 32.00 | 2.795 | 1 |
| 32.31 | 2.768 | 2 |
| 32.54 | 2.750 | 1 |
| 33.17 | 2.699 | 1 |
| 33.40 | 2.681 | 2 |
| 34.28 | 2.614 | 1 |
| 34.54 | 2.595 | 1 |
| 34.81 | 2.575 | 1 |
| 35.42 | 2.532 | 1 |
| 36.00 | 2.493 | 1 |
| 36.27 | 2.475 | 1 |
| 36.91 | 2.433 | 1 |
| 37.67 | 2.386 | 1 |
| 37.92 | 2.371 | 1 |
| 43.33 | 2.086 | 1 |
| 43.71 | 2.069 | 2 |

A portion of the as-calcined sample of Example 6 was dried at 500° C. for ½ hour and then subjected to hydrocarbon absorption. The results are shown below in Table 7.

TABLE 7

Hydrocarbon Absorption of EMM-17 of Example 6

| Hydrocarbon | Temperature (° C.) | Pressure (torr) | Amount absorbed (%) |
|---|---|---|---|
| n-hexane | 90 | 75 | 11.3 |
| cyclohexane | 50 | 70 | 15.8 |
| mesitylene | 100 | 2 | 3.0 |

Example 7

Synthesis of EMM-17 using 1-methyl-4-(pyrrolidin-1-yl)pyridinium hydroxide

A gel of stoichiometry: 0.5 HF: 0.5 SDA-OH: $SiO_2$: 4 $H_2O$, where SDA-OH is 1-methyl-4-(pyrrolidin-1-yl)pyridinium hydroxide, was prepared according to the following procedure. 13.59 g tetramethylorthosilicate was combined with 39.48 g of a 20.38 wt. % aqueous solution of 1-methyl-4-(pyrrolidin-1-yl)pyridinium hydroxide and stirred for 15 minutes. 1.93 g of a 46.3 wt. % aqueous solution of hydrofluoric acid was then added. The resulting gel was stirred and left to evaporate to the desired water ratio. The gel was then transferred to a 46 ml Teflon lined autoclave and reacted at 160° C. for 5 days in a tumbling (30-40 rpm) oven. The resulting product was recovered by filtration, washed thoroughly with deionized water, and dried in an oven at 100° C. Phase analysis by powder X-ray diffraction showed the synthesized product of Example 7 to be similar to that of Example 5.

Example 8

Synthesis of EMM-17 using 1-ethyl-4-(pyrrolidin-1-yl)pyridinium hydroxide

A gel of stoichiometry: 0.5 HF: 0.5 SDA-OH: $SiO_2$: $4H_2O$, where SDA-OH is 1-ethyl-4-(pyrrolidin-1-yl)pyridinium hydroxide, was prepared according to the following procedure. 2.70 g tetramethylorthosilicate was combined with 10.01 g of a 17.19 wt. % aqueous solution of 1-ethyl-4-(pyrrolidin-1-yl)pyridinium hydroxide and stirred for 15 minutes. 0.38 g of a 46.3 wt. % aqueous solution of hydrofluoric acid was then added. The resulting gel was stirred and left to evaporate to the desired water ratio. The evaporated gel was transferred to a 23 ml Teflon lined autoclave and reacted at 160° C. for 5 days in a tumbling (30-40 rpm) oven. The resulting product was recovered by filtration, washed thoroughly with deionized water, and dried in an oven at 100° C. Phase analysis by powder X-ray diffraction showed the synthesized product of Example 8 to be similar to that of Example 5.

Example 9

Synthesis of EMM-17 using 1-propyl-4-(pyrrolidin-1-yl)pyridinium hydroxide

A gel of stoichiometry: 0.5 HF: 0.5 SDA-OH: $SiO_2$: 4 $H_2O$, where SDA-OH is 1-propyl-4-(pyrrolidin-1-yl)pyridinium hydroxide, was prepared according to the following procedure. 4.34 g tetramethylorthosilicate was combined with 15.05 g of a 19.72 wt. % aqueous solution of 1-propyl-4-(pyrrolidin-1-yl)pyridinium hydroxide and stirred for 15 minutes. 0.62 g of a 46.3 wt. % aqueous solution of hydrofluoric acid was then added. The resulting gel was stirred and left to evaporate to the desired water ratio. The evaporated gel was then transferred to a 23 ml Teflon lined autoclave and reacted at 160° C. for 5 days in a tumbling (30-40 rpm) oven. The resulting product was recovered by filtration, washed thoroughly with deionized water, and then dried at 100° C. in an oven. Phase analysis by powder X-ray diffraction showed the synthesized product of Example 9 to be similar to that of Example 5.

Example 10

Synthesis of EMM-17 using
1-butyl-4-(pyrrolidin-1-yl)pyridinium hydroxide

A gel of stoichiometry: 0.5 HF: 0.5 SDA-OH: $SiO_2$: 4 $H_2O$, where SDA-OH is 1-butyl-4-(pyrrolidin-1-yl)pyridinium hydroxide, was prepared according to the following procedure. 5.72 g tetramethylorthosilicate was combined with 13.46 g of a 31.04 wt. % aqueous solution of 1-butyl-4-(pyrrolidin-1-yl)pyridinium hydroxide and stirred for 15 minutes. 0.81 g of a 46.3 wt. % aqueous solution of hydrofluoric acid was then added. The resulting gel was stirred and left to evaporate to the desired water ratio. The evaporated gel was then transferred to a 23 ml Teflon lined autoclave and reacted at 160° C. for 5 days in a tumbling (30-40 rpm) oven. The resulting product was recovered by filtration, washed thoroughly with deionized water, and then dried at 100° C. in an oven. Phase analysis by powder X-ray diffraction showed the synthesized product of Example 10 to be similar to that of Example 5.

Example 11

Synthesis of aluminum-containing EMM-17 with a $SiO_2/Al_2O_3$ ratio of about 100 using
1-ethyl-4-(pyrrolidin-1-yl)pyridinium hydroxide A gel of stoichiometry: 0.5 HF: 0.5 SDA-OH: 0.005 $Al_2O_3$: $SiO_2$: $4H_2O$, where SDA-OH is 1-ethyl-4-(pyrrolidin-1-yl)pyridinium hydroxide, was prepared according to the following procedure. 12.6 g tetramethylorthosilicate, 42.08 g of a 19.11 wt. % aqueous solution of 1-ethyl-4-(pyrrolidin-1-yl)pyridinium hydroxide, and 3.53 g of 5 wt. % aqueous solution of aluminum nitrate were combined and stirred for 15 minutes. 1.79 g of a 46.3 wt. % aqueous solution of hydrofluoric acid was then added. The resulting gel was stirred and left to evaporate to the desired water ratio. About one third of the evaporated gel was then transferred to a 23 ml Teflon lined autoclave and reacted in a tumbling (30-40 rpm) oven at 150° C. for 10 days. The resulting product was recovered by filtration, washed thoroughly with deionized water, and then dried at 100° C. in an oven. Phase analysis by powder X-ray diffraction showed the synthesized product of Example 11 to be similar to that of Example 5.

Example 12

About one third of the evaporated gel from Example 11 was reacted in a tumbling (30-40 rpm) oven at 160° C. for 5 days. Phase analysis by powder X-ray diffraction showed the synthesized product of Example 12 to be similar to that of Example 5.

Example 13

About one third of the evaporated gel from Example 7 was reacted in a tumbling (30-40 rpm) oven at 170° C. for 5 days. Phase analysis by powder X-ray diffraction showed the synthesized product of Example 13 to be similar to that of Example 5 but with a small amount of ZSM-22.

Example 14

Synthesis of aluminum-containing EMM-17 with a $SiO_2/Al_2O_3$ ratio of about 100 using
1-propyl-4-(pyrrolidin-1-yl)pyridinium hydroxide A gel of stoichiometry: 0.5 HF: 0.5 SDA-OH: 0.005 $Al_2O_3$: $SiO_2$: $4H_2O$, where SDA-OH is 1-propyl-4-(pyrrolidin-1-yl)pyridinium hydroxide, was prepared according to the following procedure. 14.85 g tetramethylorthosilicate, 42.95 g of a 19.11 wt. % aqueous solution of 1-propyl-4-(pyrrolidin-1-yl)pyridinium hydroxide, and 9.31 g of a 53.4 wt. % aluminum hydroxide were combined and stirred for 15 minutes. 2.11 g of a 46.3 wt. % aqueous solution of hydrofluoric acid was then added. The resulting gel was stirred and left to evaporate to the desired water ratio. About one third of the evaporated gel was then transferred to a 23 ml Teflon lined autoclave and reacted in a tumbling (30-40 rpm) oven at 150° C. for 10 days. The resulting product was recovered by filtration, washed thoroughly with deionized water, and then dried at 100° C. in an oven. Phase analysis by powder X-ray diffraction showed the synthesized product of Example 14 to be similar to that of Example 5.

Example 15

About one third of the evaporated gel from Example 14 was transferred to a 23 ml Teflon lined autoclave and reacted in a tumbling (30-40 rpm) oven at 160° C. for 5 days. The resulting product was recovered by filtration, washed thoroughly with deionized water, and then dried at 100° C. in an oven. Phase analysis by powder X-ray diffraction showed the synthesized product of Example 15 to be similar to that of Example 5.

Example 16

About one third of the evaporated gel from Example 14 was transferred to a 23 ml Teflon lined autoclave and reacted in a tumbling (30-40 rpm) oven at 170° C. for 5 days. The resulting product was recovered by filtration, washed thoroughly with deionized water, and then dried at 100° C. in an oven. Phase analysis by powder X-ray diffraction showed the synthesized product of Example 16 to be similar to that of Example 5.

Example 17

Calcination of the EMM-17 Synthesized in Example 12

A 1.863 g sample of EMM-17 from Example 12 was calcined in a furnace by heating at 400° C. in $N_2$ for 1 hour followed by heating at 600° C. in air for 5 hours to give 1.515 g of white solid. Phase analysis by powder X-ray diffraction showed the sample to be similar to that of FIG. 2. Elemental analysis by ICP-AES (Inductively Coupled Plasma—Atomic Emission Spectroscopy) after dissolution in aqueous HF solution gave 95.2% $SiO_2$, 1.01% $Al_2O_3$, 0.0334% Na and 0.0185% K for a $SiO_2/Al_2O_3$ ratio of 160.

Example 18

Synthesis of aluminum-containing EMM-17 with a $SiO_2/Al_2O_3$ ratio of about 80 using
1-ethyl-4-(pyrrolidin-1-yl)pyridinium hydroxide A gel of stoichiometry: 0.5 HF: 0.5 SDA-OH: 0.0625 $Al_2O_3$: $SiO_2$: $4H_2O$, where SDA-OH is 1-ethyl-4-(pyrrolidin-1-yl)pyridinium hydroxide, was prepared according to the following procedure. 3.21 g Degussa Ultrasil VN3PM, 22.86 g of a 22.22 wt. % aqueous solution of 1-ethyl-4-(pyrrolidin-1-yl)pyridinium hydroxide, and 0.80 g of 27.8 wt. % aqueous solution of aluminum sulfate were combined and stirred for 15 minutes. 2.96 g of a 30 wt. % aqueous solution of ammonium fluoride was then added, followed by 0.16 g of EMM-17 seeds. The resulting gel was stirred and left to evaporate to the desired water ratio. The evaporated gel was then transferred to a 23 ml Teflon lined autoclave and reacted in a tumbling (30-40 rpm) oven at 160° C. for 7 days. The resulting product was recovered by filtration, washed thoroughly with deionized water, and then dried at 100° C. in an oven. Phase analysis by powder X-ray diffraction showed the synthesized product of Example 18 to be similar to that of Example 5.

Example 19

Synthesis of aluminum-containing EMM-17 with a $SiO_2/Al_2O_3$ ratio of about 50 using 1-ethyl-4-(pyrrolidin-1-yl)pyridinium hydroxide A gel of stoichiometry: 0.5 HF: 0.5 SDA-OH: 0.01 $Al_2O_3$: $SiO_2$: $4H_2O$, where SDA-OH is 1-ethyl-4-(pyrrolidin-1-yl)pyridinium hydroxide, was prepared according to the following procedure. 3.16 g Degussa Ultrasil VN3PM, 22.5 g of a 22.22 wt. % aqueous solution of 1-ethyl-4-(pyrrolidin-1-yl)pyridinium hydroxide, and 1.27 g of 27.8 wt. % aqueous solution of aluminum sulfate were combined and stirred for 15 minutes. 2.92 g of a 30 wt. % aqueous solution of ammonium fluoride was then added, followed by 0.16 g of EMM-17 seeds. The resulting gel was stirred and left to evaporate to the desired water ratio. The evaporated gel was then transferred to a 23 ml Teflon lined autoclave and reacted in a tumbling (30-40 rpm) oven at 160° C. for 13 days. The resulting product was recovered by filtration, washed thoroughly with deionized water, and then dried at 100° C. in an oven. Phase analysis by powder X-ray diffraction showed the synthesized product of Example 19 to be similar to that of Example 5.

Example 20

Synthesis of aluminum-containing EMM-17 with a $SiO_2/Al_2O_3$ ratio of about 30 using 1-ethyl-4-(pyrrolidin-1-yl)pyridinium hydroxide A gel of stoichiometry: 0.5 HF: 0.5 SDA-OH: 0.0167 $Al_2O_3$: $SiO_2$: $4H_2O$, where SDA-OH is 1-ethyl-4-(pyrrolidin-1-yl)pyridinium hydroxide, was prepared according to the following procedure. 3.07 g Degussa Ultrasil VN3PM, 21.88 g of a 22.22 wt. % aqueous solution of 1-ethyl-4-(pyrrolidin-1-yl)pyridinium hydroxide, and 2.05 g of 27.8 wt. % aqueous solution of aluminum sulfate were combined and stirred for 15 minutes. 2.84 g of a 30 wt. % aqueous solution of ammonium fluoride was then added, followed by 0.16 g of EMM-17 seeds. The resulting gel was stirred and left to evaporate to the desired water ratio. The evaporated gel was then transferred to a 23 ml Teflon lined autoclave and reacted in a tumbling (30-40 rpm) oven at 160° C. for 34 days. The resulting product was recovered by filtration, washed thoroughly with deionized water, and then dried at 100° C. in an oven. Phase analysis by powder X-ray diffraction showed the synthesized product of Example 20 to be similar to that of Example 5.

Example 21

Synthesis of boron-containing EMM-17 with a $SiO_2/B_2O_3$ ratio of about 30 using 1-ethyl-4-(pyrrolidin-1-yl)pyridinium hydroxide A gel of stoichiometry: 0.515 HF: 0.515 SDA-OH: 0.0155 $B_2O_3$: $SiO_2$: 4.428 $H_2O$, where SDA-OH is 1-ethyl-4-(pyrrolidin-1-yl)pyridinium hydroxide, was prepared according to the following procedure. 84 µL tetramethylorthosilicate, 372 µL of a 15.04 wt. % aqueous solution of 1-propyl-4-(pyrrolidin-1-yl)pyridinium hydroxide, and 31 µL of a 3.47 wt. % boric acid were combined. The resulting gel was stirred and left to evaporate to the desired water ratio. 28 µL of a 20 wt. % aqueous solution of hydrofluoric acid was then added. The gel was then transferred to an autoclave and reacted in an oven at 160° C. for 10 days. The resulting product was recovered by filtration, washed thoroughly with deionized water, and then dried at 100° C. in an oven. Phase analysis by powder X-ray diffraction showed the synthesized product of Example 21 to be similar to that of Example 5.

Comparative Example 1

Comparing EMM-17 to NU-86

The diffraction pattern of EMM-17 is similar to NU-86 (U.S. Pat. No. 5,108,579 to Casci). To compare diffraction patterns, which were measured under different conditions (NU-86 variable slit, EMM-17 fixed slit) the calcined EMM-17 diffraction pattern was converted to variable slit data using the fixed slit→variable slit filter algorithm of MDI Jade and the peak intensities were determined from the peak heights as in U.S. Pat. No. 5,108,579. All major peaks are shown below in Table 8 for comparison. While some similarities exist between the diffraction patterns, there are also significant differences. Most notable is the peak around 5.2 degrees of two-theta, which is always present in EMM-17, but never seen in NU-86.

TABLE 8

X-Ray Diffraction Patterns of EMM-17 and NU-86

| | EMM-17 | | NU-86 (Example 1 of U.S. Pat. No. 5,108,579) | |
|---|---|---|---|---|
| 2Θ | d (Å) | Relative Intensity | d (Å) | Relative Intensity |
| 5.19 | 17.0 | W | | |
| 7.61 | 11.6 | Vs | 11.8 | w-m |
| 8.05 | 11.0 | M | 11.1 | w-m |
| 8.38 | 10.54 | S | 11.65 | w |
| 10.39 | 8.5 | Vs | 8.6 | w |
| 14.69 | 6.02 | W | | |
| 15.65 | 5.66 | M | | |
| 21.16 | 4.20 | M | 4.22 | m |
| 21.47 | 4.14 | W | 4.15 | m |
| 21.89 | 4.06 | W | 4.1 | w-m |
| 22.65 | 3.92 | Vs | 3.94 | vs |
| 22.79 | 3.90 | M | 3.88 | s-vs |
| 23.19 | 3.83 | S | | |
| 23.89 | 3.72 | M | 3.74 | m |
| 24.00 | 3.71 | M | | |
| 24.26 | 3.67 | W | | |
| 25.25 | 3.52 | M | | |
| 25.83 | 3.45 | W | 3.45 | w |
| 26.65 | 3.34 | W | 3.35 | w |
| 28.86 | 3.09 | W | 3.11 | w |
| 43.72 | 2.07 | W | 2.07 | w |

Comparative Example 2

Synthesis of NU-86 Based on Example 8 of U.S. Pat. No. 5,108,579

Figure 3:
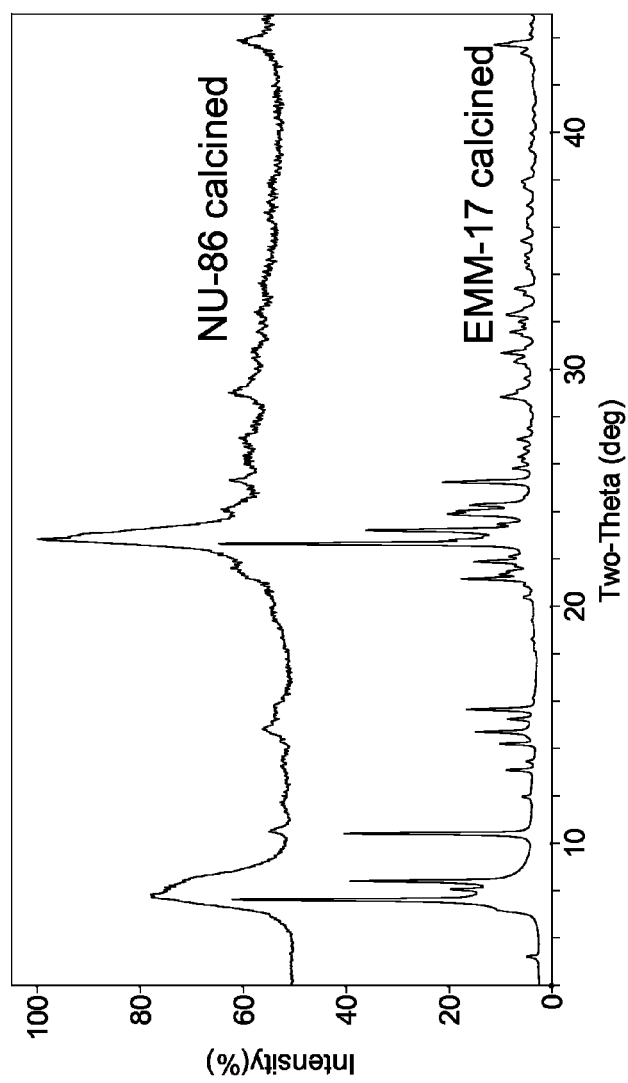
FIG. 3 provides a comparison of the X-ray diffraction patterns of calcined NU-86 and calcined EMM-17.

A gel of stoichiometry: 15 octamethonium dibromide: 12$Na_2O$: 1.846$Al_2O_3$: 60 $SiO_2$: 3000$H_2O$ was prepared from fumed silica solution (CAB-O-SPERSE), sodium aluminate solution, sodium hydroxide and octamethonium dibromide. The mixture was placed in a 300 ml stirred autoclave (300 rpm) for 23 days at 165° C. The product was recovered by filtration, washed with deionized water, and dried in an air oven. Phase analysis by powder X-ray diffraction showed the product to be pure NU-86. A portion of the NU-86 was calcined in air at 600° C. to remove the template. Phase analysis by powder X-ray diffraction showed the calcined sample to be fully crystalline. A comparison of the diffraction patterns of calcined NU-86 and calcined EMM-17 (converted to variable slit intensities) is shown in FIG. 3.

It will be appreciated that various presently unforeseen or unanticipated alternatives, modifications, variations or improvements therein may be subsequently made by those skilled in the art, and are also intended to be encompassed by the following claims.

The disclosures of the foregoing publications are hereby incorporated by reference in their entirety. The appropriate components and aspects of the foregoing publications may also be selected for the present materials and methods in embodiments thereof.

The invention claimed is:

1. A molecular sieve material having, in its as-calcined form, an X-ray diffraction pattern including the following peaks in Table 9:

TABLE 9

| d-spacing (Å) | Relative Intensity [100 × I/I(o)] % |
| --- | --- |
| 17.4–16.4 | 1–10 |
| 12.6–12.1 | 1–20 |
| 11.8–11.4 | 60–100 |
| 11.2–10.8 | 5–30 |
| 10.7–10.3 | 30–80 |
| 8.62–8.38 | 10–40 |
| 6.09–5.96 | 1–20 |
| 5.71–5.61 | 1–20 |
| 4.23–4.17 | 1–20 |
| 4.09–4.03 | 1–10 |
| 3.952–3.901 | 10–40 |
| 3.857–3.809 | 5–30 |
| 3.751–3.705 | 1–20 |
| 3.727–3.682 | 1–20 |
| 3.689–3.644 | 1–10 |
| 3.547–3.506 | 1–20. |

2. The molecular sieve material of claim 1 having a composition comprising the molar relationship:

(n)YO$_2$:X$_2$O$_3$, wherein n is at least 30, X is a trivalent element, and Y is a tetravalent element.

3. The molecular sieve material of claim 2, wherein X includes one or more of B, Al, Fe, and Ga and Y includes one or more of Si, Ge, Sn, Ti, and Zr.

4. The molecular sieve material of claim 2, wherein X is aluminum and Y is silicon.

5. A molecular sieve material having, in its as-synthesized form, an X-ray diffraction pattern including the following peaks in Table 10:

TABLE 10

| d-spacing (Å) | Relative Intensity [100 × I/I(o)] % |
| --- | --- |
| 17.3–16.4 | 1–10 |
| 11.8–11.3 | 60–100 |

TABLE 10-continued

| d-spacing (Å) | Relative Intensity [100 × I/I(o)] % |
| --- | --- |
| 11.1–10.7 | 60–100 |
| 10.7–10.3 | 30–100 |
| 8.58–8.34 | 30–80 |
| 4.21–4.15 | 10–40 |
| 4.17–4.11 | 5–30 |
| 4.07–4.01 | 10–40 |
| 3.951–3.899 | 60–100 |
| 3.922–3.871 | 10–40 |
| 3.832–3.784 | 50–90 |
| 3.737–3.691 | 10–40 |
| 3.704–3.659 | 10–40 |
| 3.677–3.632 | 5–30 |
| 3.537–3.496 | 10–40 |
| 2.077–2.063 | 5–30. |

6. The molecular sieve material of claim 5 having a composition comprising the molar relationship:

kF:mQ:(n)YO$_2$: X$_2$O$_3$, wherein 0≤k≤1.0, 0<m≤1.0, n is at least 30, F is a source of fluoride, Q is an organic structure directing agent, X is a trivalent element and Y is a tetravalent element.

7. The molecular sieve material of claim 6, wherein X is aluminum and Y is silicon.

8. The molecular sieve material of claim 6, wherein X includes one or more of B, Al, Fe, and Ga and Y includes one or more of Si, Ge, Sn, Ti, and Zr.

9. The molecular sieve material of claim 6, wherein Q is selected from the group consisting of 1-methyl-4-(pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations and mixtures thereof.

10. A process for producing the molecular sieve material of claim 6, the process comprising the steps of:
(a) preparing a synthesis mixture capable of forming said material, said mixture comprising water, a source of hydroxyl ions, a source of an oxide of a tetravalent element Y, a source of a trivalent element X, optionally a source of fluoride ions, and a directing agent Q selected from the group consisting of 1-methyl-4-(pyrrolidin-1-yl)pyridinium cations, 1-ethyl-4-(pyrrolidin-1-yl)pyridinium cations, 1-propyl-4-(pyrrolidin-1-yl) pyridinium cations, 1-butyl-4-(pyrrolidin-1-yl) pyridinium cations and mixtures thereof, and said synthesis mixture having a composition, in terms of mole ratios, in the following amounts and/or ranges:

YO$_2$/X$_2$O$_3$ at least 30;

H$_2$O/YO$_2$ 4 to 10;

OH$^-$/YO$_2$ 0.1 to 1;

F/YO$_2$ 0 to 1; and

Q/YO$_2$ 0.1 to 1;

(b) heating said synthesis mixture under crystallization conditions including a temperature of from about 100° C. to about 200° C. and a time from about 1 to about 28 days until crystals of said material are formed; and
(c) recovering said crystalline material from step (ii).

11. The process of claim 10, wherein the source of fluoride ions is one or more of HF, NH$_4$F, and NH$_4$HF$_2$.

12. A process for synthesizing a crystalline molecular sieve material comprising the steps of:

(a) providing a synthesis mixture capable of forming the crystalline molecular sieve material, said synthesis mixture comprising water, a source of hydroxyl ions, a source of an oxide of a tetravalent element Y, a source of a trivalent element X, optionally a source of fluoride ions and an organic directing agent Q selected from the group consisting of 1-methyl-4-(pyrrolidin-1-yl)pyridinium cations, 1-ethyl-4-(pyrrolidin-1-yl)pyridinium cations, 1-propyl-4-(pyrrolidin-1-yl)pyridinium cations, 1-butyl-4-(pyrrolidin-1-yl)pyridinium cations and mixtures thereof; and (b) heating said synthesis mixture under crystallization conditions until crystals of said molecular sieve material are formed containing said organic directing agent Q within the crystalline structure of the molecular sieve material.

13. The process of claim 12, wherein said synthesis mixture in step (a) has a composition, in terms of mole ratios, in the following amounts and/or ranges:

$YO_2/X_2O_3$ at least 30;

$H_2O/YO_2$ 4 to 10;

$OH^-/YO_2$ 0.1 to 1;

$F/YO_2$ 0 to 1; and $Q/YO_2$ 0.1 to 1.

14. The process of claim 13, wherein said crystallization conditions include a temperature of from about 100° C. to about 200° C. and a time from about 1 to about 28 days.

15. The process of claim 14, further comprising the step of:

(c) recovering said crystalline material from step (b).

* * * * *